United States Patent [19]

Sage et al.

[11] Patent Number: 5,801,294
[45] Date of Patent: Sep. 1, 1998

[54] PROCESS FOR THE PURIFICATION OF SATURATED HYDROFLUOROCARBONS

[75] Inventors: Jean-Marc Sage, Oullins; Eric Lacroix, Amberieux D'Azergues, both of France

[73] Assignee: Elf Atochem S.A., France

[21] Appl. No.: 869,948

[22] Filed: Jun. 5, 1997

[30] Foreign Application Priority Data

Jun. 6, 1996 [FR] France ................. 96 06992

[51] Int. Cl.⁶ .................................................. C07C 17/20
[52] U.S. Cl. .................................................. 570/177
[58] Field of Search .................................................. 570/177

[56] References Cited

U.S. PATENT DOCUMENTS

| | | | |
|---|---|---|---|
| 3,004,908 | 10/1961 | Haszeldine | 204/157.93 |
| 5,001,287 | 3/1991 | Fernanadez | 570/178 |
| 5,326,918 | 7/1994 | Correia et al. | 570/177 |
| 5,430,205 | 7/1995 | Cheminal et al. | 570/177 |

FOREIGN PATENT DOCUMENTS

| | | |
|---|---|---|
| 389334 | 9/1922 | European Pat. Off. . |
| 357328 | 3/1990 | European Pat. Off. . |
| 508631 | 10/1992 | European Pat. Off. . |
| 370688 | 7/1994 | European Pat. Off. . |
| 548744 | 7/1995 | European Pat. Off. . |
| 2698094 | 5/1994 | France . |
| 5-000972 | 1/1993 | Japan . |
| 0500973 | 10/1993 | Japan . |
| 6-80592 | 3/1994 | Japan . |

OTHER PUBLICATIONS

French Search Report dated Jan. 22, 1997.

*Primary Examiner*—Ceila Chang
*Assistant Examiner*—Garth M. Dahlen
*Attorney, Agent, or Firm*—Bell, Boyd & Lloyd

[57] ABSTRACT

In order to remove olefinic impurities present in a hydrofluorocarbon such as pentafluoroethane (R-125), the impure hydrofluorocarbon is treated with oxygen in the absence of catalyst or of active charcoal.

The process is well suited to the purification of fluoroethanes and, more particularly, to that of pentafluoroethane.

17 Claims, No Drawings

PROCESS FOR THE PURIFICATION OF SATURATED HYDROFLUOROCARBONS

FIELD OF THE INVENTION

The present invention relates to the field of halogenated hydrocarbons and more particularly to the purification of hydrofluorocarbons, known in the trade under the name HFC. These compounds, such as, for example, pentafluoroethane (R-125) and 1,1,1,2 tetrafluoroethane (R-134a) are currently being developed in order to replace the CFCs (chlorofluorocarbons) which, such as for example dichlorodifluoromethane (R-12) are suspected of contributing to the depletion of the ozone layer.

BACKGROUND OF THE INVENTION

The manufacture of a hydrofluorocarbon, for example by fluorination of a $C_2$ compound by means of hydrofluoric acid, of course requires suitable catalysts and operating conditions but it is also generally necessary to consider the purification of the final product. This is because, although they result in high yields and selectivities, the processes and catalysts employed during the synthesis of HFC compounds generate impurities which are often difficult to separate or remove by conventional means, such as distillation or the selective dissolution of these impurities in an appropriate solvent. Moreover, even when present in a low amount, some of these impurities have to be removed because of their toxicity. Mention may more particularly be made, among these impurities, of olefinic derivatives and in particular of those containing two carbon atoms and variable proportions of hydrogen, fluorine and/or chlorine atoms.

Various methods which make it possible to remove olefinic impurities or to reduce the content thereof have already been described in the prior art. Thus, the olefin 2-chloro-1, 1-difluoroethylene (R-1122), contained in an R-134a, can be removed by passing over an active charcoal (Patent EP 389 334) or by treatment with a metal hydride in tetrahydrofuran (Patent EP 508 631).

In order to remove the olefins $CF_3$—$CCl$=$CCl$—$CF_3$, $CF_3$—$CCl$=$CH$—$CF_3$, $CCl_2$=$CF_2$ and $CF_2$=$CFCl$ present as impurities in a 1,1-dichloro-2,2,2-trifluoroethane (R-123), provision has been made, in Patent EP 357 328, to treat the R-123 with a basic aqueous potassium permanganate solution.

In Patent EP 370 688, the content of olefinic impurities in an HFC or HCFC (hydrochlorofluorocarbon) compound is reduced by passing over a metal oxide bed composed of at least one Cu(II), Co(II), Ag(I) or Mn(II) oxide at a temperature of between 20° and 300° C.

U.S. Pat. No. 5,001,287 has recommended the catalytic hydrogenation of olefinic impurities by passing the impure HFC compound over a catalyst, such as Pd/C, in the presence of hydrogen.

Patent EP 548,744 has provided for the treatment of the HFC or HCFC compound to be purified by means of fluorine at a temperature of the order of −80° to −40° C. However, the use of fluorine in its $F_2$ diatomic form is very difficult industrially because of the dangers related to the very high reactivity of fluorine, which necessitates diluting it to a very high degree in nitrogen.

The removal of an olefin can also be carried out by photooxidation. This method, in which the product to be purified is irradiated with radiation of UV type in the presence of oxygen, is described for example in Patent FR 2,698,094 for the purification of a 1,1-dichloro-1-fluoroethane (R-141b).

U.S. Pat. No. 5,430,205 has provided for the removal of olefinic impurities of an R-134a by passing a gaseous mixture of crude R-134a, hydrofluoric acid and oxygen or air over a fluorination catalyst at a temperature of between 200° and 300° C. However, under these conditions, the R-134a and its precursor, R-133a (1-chloro-2,2,2-trifluoroethane), can undergo partial combustion, resulting in a loss in productivity.

It is also known (JP 06 080 592) to remove halogenated impurities contained in an HCFC by passing it, in the gas phase, over an active charcoal in the presence of oxygen at a temperature of between 80° and 300° C. However, when large amounts of impurities are present, the active charcoal has to be frequently regenerated.

According to Patent Application JP 05 000 972, ozone is used to purify HCFCs or HFCs. However, ozone exhibits the disadvantage of being a toxic gas which, even at relatively low content in the surrounding atmosphere, can cause problems with respect to human health.

DESCRIPTION OF THE INVENTION

It has now been found that the introduction of oxygen (pure or in the form of air) into an HFC compound makes it possible to remove virtually all olefinic impurities therefrom, in particular $C_2$ olefins and more particularly chlorotrifluoroethylene. This removal does not require the presence of a catalyst or of an active charcoal. It takes place at a moderate temperature and can be carried out in the liquid phase, which is particularly advantageous from an industrial viewpoint. Thus, by simple addition of an appropriate amount of oxygen, an olefin such as chlorotrifluoroethylene (R-1113 or CTFE) can be completely removed from an HFC, such as R-125.

The subject of the invention is thus a process for the purification of an HFP compound containing at least one olefinic impurity, characterized in that it comprises a stage which consists in bringing the said impure HFC into contact with oxygen, in the absence of catalyst or of active charcoal.

In an HFC compound to be purified, the content of olefin(s) by weight is generally between 10 and 10,000 ppm, most often between 10 and 1000 ppm. Although, it is more particularly targeted at the purification of fluoroethanes containing from 2 to 5 fluorine atoms and preferentially that of R-125, the treatment with oxygen according to the invention can also be applied to purify an HFC compound containing 3 or more than 3 carbon atoms.

The amount of oxygen to be added to the HFC compound to be purified can reach from 10 to 10,000 ppm by weight and is preferably between 500 and 5000 ppm. It obviously depends on the content of olefin(s) in the product to be purified and on the temperature and pressure conditions employed. Generally, it is advisable to use an amount of oxygen such that the oxygen/olefin(s) molar ratio is between 1 and 1000, preferably between 1 and 200 and, more particularly, between 1 and 50.

The oxygen can be introduced into the HFC compound to be purified continuously or non-continuously, either in the form of pure oxygen or diluted in another gas, such as nitrogen, for example in the form of air.

The duration of the treatment can vary within wide limits (a few minutes to several days). This is because it depends on the content of olefin(s) to be removed, on the amount of oxygen added and on the temperature and presure conditions employed. The operation can be carried out at a temperature ranging from −40° to +200° C., preferably between 10° and 150° C. and, advantageously, around room temperature. The pressure can range from 10 to 10,000 kPa but is preferably between 500 and 5000 kPa.

The treatment according to the invention can be implemented in the liquid phase or in the gas phase but it is preferable, from a practical viewpoint, to carry out the treatment in the liquid phase.

After the treatment according to the invention, the HFC compound which has been freed from its olefinic impurities can obviously be subjected to another purification stage in order to remove the other impurities initially present and/or the products generated during the treatment with oxygen according to the invention, such as HF, HCl, $CF_3COOH$, $COF_2$, COFCl or $COCl_2$ residues. This other stage can comprise, for example, washing with an aqueous alkaline solution or passing over an active charcoal, in particular an alkaline active charcoal.

EXAMPLES

The following examples illustrate the invention without limiting it. The ppm values are expressed by weight, except when otherwise mentioned.

Example 1 (Comparative)

2.0 g of pentafluoroethane (R-125), containing 450 ppm of chlorotrifluoroethylene (R-1113), 10,000 ppm of chloropentafluoroethane (R-115), 285 ppm of 1,1,1trifluoroethane (R-143a) and 100 ppm of 1-chloro1,2,2,2-tetrafluoroethane (R-124), are introduced, in the absence of air by trapping with liquid nitrogen, into a glass tube with a volume of approximately 8 ml. The tube, maintained under vacuum and at a temperature of liquid nitrogen, is subsequently sealed, then introduced into a heating apparatus excluded from the light and agitated by rocking. The temperature is brought to 80° C. for 48 hours.

At the end of this period of time, the sealed tube is cooled to the temperature of liquid nitrogen and connected to a steel bottle (volume: 20 ml) which has been placed under vacuum beforehand and maintained at the temperature of liquid nitrogen. The top of the tube is subsequently broken and the tube is gently reheated to room temperature in order to recover the gases by trapping in the metal test tube.

2 g of gas are thus recovered in the test tube, the VPC analysis of which shows that the composition of the R-125 has remained virtually unchanged.

EXAMPLE 2

The procedure is carried out as in Example 1 with the same R-125 but by adding 2700 ppm of oxygen to the 2 g of R-125, i.e. 1% by volume with respect to the gaseous R-125.

After reacting for 48 hours, analysis of the recovered R-125 shows that the R-1113 content has fallen below 3 ppm, the initial contents of R-115, R-143a and R-124 having remained unchanged.

EXAMPLE 3

0.5% by volume of air (i.e. 270 ppm of oxygen) is added to an impure R-125 containing 13 ppm of R-1113, 20 ppm of R-143a and 675 ppm of R-134a and then the impure R-125 is stored in a receptacle made of zinc-plated sheet metal for 30 days at room temperature (10° to 20° C.) and at an absolute pressure of 1200 kPa.

At the end of this period of time, analysis of the product shows that its R-1113 content has become less than 1 ppm, the R-143a and R-134a contents having remained virtually unchanged.

The product can subsequently be passed over an active charcoal in order to free it from traces of acidity formed during the treatment.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the purification of a hydrofluorocarbon (HFC) containing at least one olefinic impurity, comprising a stage which consists in bringing the impure HFC into contact with oxygen, in the absence of catalyst or of active charcoal.

2. Process according to claim 1, wherein the olefinic impurity is a $C_2$ olefin.

3. Process according to claim 1, wherein the olefinic impurity is a $C_2$ olefin.

4. Process according to claim 1, wherein the treatment is carried out at a temperature ranging from −40° to +200° C.

5. Process according to claim 1, wherein the treatment is carried out at a pressure of between 10 and 10,000 kPa.

6. Process according to one of claim 1 wherein the process is carried out in the liquid phase.

7. Process according to claim 1, wherein the oxygen is introduced in the form of air.

8. Method for purification of a fluoroethane containing from 2 to 5 fluorine atoms comprising the purification stage according to claim 1.

9. Method for the removal of chlorotrifluoroethylene present in a hydrofluorocarbon, optionally in a fluoroethane containing from 2 to 5 fluorine atoms comprising the process according to claim 1.

10. Method for the removal of chlorotrifluoroethylene present in a pentafluoroethane comprising the process according to claim 1.

11. Process according to claim 2, wherein the olefinic impurity is chlorotrifluoroethylene.

12. Process according to claim 3, wherein the molar ratio is between 1 and 200.

13. Process according to claim 12, wherein the molar ratio is between 1 and 50.

14. Process according to claim 4, wherein the temperature is between 10° and 150° C.

15. Process according to claim 4, wherein the temperature is about room temperature.

16. The process according to claim 5, wherein the pressure is between 500 and 5000 kPa.

17. Process according to claim 8, wherein the fluoroethane is pentafluoroethane.

* * * * *